US006375673B1

(12) United States Patent
Clifton et al.

(10) Patent No.: US 6,375,673 B1
(45) Date of Patent: *Apr. 23, 2002

(54) HEAT TRANSFER BLANKET FOR AND METHOD OF CONTROLLING A PATIENT'S TEMPERATURE

(75) Inventors: Guy L. Clifton; Emmy R. Miller, both of Houston, TX (US)

(73) Assignee: The Board of Regents of the University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/197,297

(22) Filed: Nov. 20, 1998

Related U.S. Application Data

(63) Continuation-in-part of application No. 09/065,165, filed on Apr. 23, 1998, now Pat. No. 6,113,626.

(51) Int. Cl.[7] .................................................. A61F 7/00
(52) U.S. Cl. ........................................ 607/104; 607/108
(58) Field of Search ......................... 607/96, 104, 108, 607/112; 602/13, 14, 19, 26

(56) References Cited

U.S. PATENT DOCUMENTS

| | | | | | |
|---|---|---|---|---|---|
| 4,353,359 A | * | 10/1982 | Milbauer | ..................... | 128/66 |
| 4,718,429 A | * | 1/1988 | Smidt et al. | ................. | 128/400 |
| 4,753,240 A | * | 6/1988 | Sparks | ......................... | 128/379 |
| 5,074,288 A | * | 12/1991 | Miller | ......................... | 128/78 |
| 5,417,720 A | * | 5/1995 | Mason | ......................... | 607/104 |
| 5,443,488 A | * | 8/1995 | Namenye et al. | ........... | 607/104 |
| 5,503,621 A | * | 4/1996 | Miller | .......................... | 602/19 |
| 5,537,690 A | * | 7/1996 | Johnson | ........................... | 2/44 |
| 5,683,439 A | * | 11/1997 | Jensen | ........................ | 607/104 |
| 5,718,670 A | * | 2/1998 | Bremer | ......................... | 602/19 |
| 5,800,491 A | * | 9/1998 | Kolen et al. | ................. | 607/108 |
| 5,871,526 A | * | 2/1999 | Gibbs et al. | ................. | 607/104 |
| 5,891,187 A | * | 4/1999 | Winthrop et al. | ............. | 607/96 |
| 6,048,326 A | * | 4/2000 | Davis et al. | .................. | 602/26 |
| 6,113,626 A | * | 9/2000 | Clifton et al. | ................ | 607/96 |

OTHER PUBLICATIONS

Published International Patent Application; PCT/IL99/00059; International Publication Date Sep. 10, 1999; MTRE Advanced Technology Ltd.; System And Method For Heat Control Of A Living Body.

* cited by examiner

Primary Examiner—Linda C. M. Dvorak
Assistant Examiner—Jocelyn Ram
(74) Attorney, Agent, or Firm—Hodgson Russ LLP

(57) ABSTRACT

The present invention relates to heat transfer blankets which wrap the torso and legs leaving the arms, buttocks, perineum and head exposed and allow for the selective heating or cooling of various body parts at the same or different rates. The blankets of the present invention are also made up of panels, which may include foldable extensions to allow coverage of a wider range of body sizes, which may be selectively opened to gain access to the chest, abdomen, legs or back to expose a surgical field or to provide access to these areas for necessary medical care.

12 Claims, 11 Drawing Sheets

HEAT TRANSFER BLANKET FOR AND METHOD OF CONTROLLING A PATIENT'S TEMPERATURE

RELATED APPLICATION DATA

This application is a continuation-in-part of U.S. application Ser. No. 09/065,156 filed Apr. 23, 1998 now U.S. Pat. No. 6,113,626.

BACKGROUND OF THE INVENTION

1. Field of the Invention

The present invention relates to a heat transfer system for and method of controlling a patient's temperature. In another aspect, the present invention relates to a heat transfer blanket for and method of controlling a patient's temperature. In even another aspect, the present invention relates to a heat transfer blanket for controlling a patient's temperature where in the heat transfer blanket comprises independently controlled zones for heating and cooling, and a method for heating and cooling various parts of a patient at different temperatures and rates.

2. Description of the Related Art

Man is considered to be a tropical animal, with normal functioning requiring a body temperature of about 37° C. Relying only upon that protection from temperature stress which is provided physiologically at birth, comfortable human survival would require an environment of 37° C., +/– perhaps 1°. See, "Hypothermia-physiology, Signs, Symptoms and Treatment Considerations", Search and Rescue Society of British Columbia, compiled by Michael McEwan, 1995. The McEwan article further notes that a body can self-compensate for small upward or downward variations in temperature through the activation of a built-in thermal regulatory system, controlled by temperature sensors in the skin.

For example, the response to an upward variation in body temperature is the initiation of perspiration, which moves moisture from body tissues to the body surface, where evaporation causes cooling. Likewise, the response to a downward variation in body temperature is shivering, which is the body's involuntary contraction and expansion of muscle tissue on a large scale in an attempt to generate heat.

Stiff and Sixta, "Hypothermia Care and Prevention", 1997, generally define hypothermia as occurring when the body's core temperature drops below its normal 37° C.

The McEwan article defines impending hypothermia as occurring when the core temperature decreases to 36° C.

In the early stages mild hypothermia causes vigorous shivering which is usually accompanied by an increase in pulse and breathing rates. Cold, white hands and feet (as the blood vessels in the skin constrict) are the first signs of blood being shunted away from the body's extremities.

The McEwan article describes mild hypothermia as occurring when the core temperature is dropped to the range of 34–35° C. At this point, uncontrolled, intense shivering begins, although the victim is still alert and able to help self, however, movements become less coordinated and the coldness is creating some pain and discomfort.

The McEwan article defines moderate hypothermia as occurring when the core temperature is in the range of 31 to 33° C. At this point shivering slows or stops, muscles begin to stiffen and mental confusion and apathy sets in. Speech becomes slow, vague and slurred with breathing becoming slower and shallower.

The McEwan article defines severe hypothermia as occurring when the core temperature is below 31° C., with Stiff and Sixta defining severe hypothermia as resulting when the body temperature drops below 33° C. Shunting of the blood continues, manifesting as bluish lips and finger tips from poor oxygenation of the tissues near the body surface. Decreased circulation as results in a build-up of acid metabolites (waste products) in the muscles of the extremities until shivering stops and is replaced by muscular rigidity. The pulse and respirations begin to slow as the body core cools to 30° C. The heart may stop at temperatures of about 28° C. or less.

Hypothermia can occur easily enough during any outdoor excursion, especially in wilderness situations where weather conditions may deteriorate unexpectedly or where travelers may become lost, injured or exhaust food supplies prematurely. Additionally, outdoor activities involving water presents the added possibility of emersion with the body cooling up to 25 times faster in water than in air.

Mild hypothermia is also a common occurrence during major surgery on the body. The usual causes of such perioperative hypothermia or anesthetic-induced impairment of thermal regulation, exposure to cold, altered distribution of body heat, and surgical exposure of the body cavity to a room temperature environment. This is particularly a problem in patients anesthetized for over two hours in where there are large incisions exposing the body's interior to room temperature. Routine measures to reduce heat loss during operation include covering the skin, warming intravenous fluid and transfused blood, and increasing ambient temperature. In most operations, with the exception of those on the brain, prevention of hypothermia is a mainstay of anesthetic management because hypothermia during surgery can adversely affect the outcome. See "Colorectal Surgery Comes in From the Cold", The New England Journal of Medicine, Vol. 334, No. 19, Mortensen, et al, May 19, 1996.

As discussed above, hypothermia may be encountered as a result of an accident or may be inadvertently acquired during major surgery. In an odd twist, hypothermia may be induced by a physician in the treatment of various conditions usually those in which the physician desires to protect the brain or heart. For example, U.S. Pat. No. 5,486,204, issued Jan. 23, 1996 to Clifton discloses a method of treating a non-penetrating head wound with hypothermia. Such a treatment protocol includes specific defined times, temperatures, rates of change of temperature and the timing of the introduction of medications, and controlled rewarming. Additionally, hypothermia is frequently induced during surgery for intra cranial aneurysms.

The McEwan article notes that treatment of cold injuries has long been controversial. It is also clear that it is not enough merely to reheat a victim suffering from hypothermia, but that controlled heating must be applied. For example, Baron Larrey, Napoleon's Chief Surgeon observed that those soldiers, suffering from hypothermia, who were placed closest to the campfire during Napoleon's retreat from Russian died. These soldiers probably rewarmed rapidly. As a general principle initial management principles for treating hypothermia emphasized prevention of further heat loss, rewarming as soon as it is safely possible at a "successful" rate (slowly) and rewarming the core before the shell in an attempt to avoid inducing lethal side effects during rewarming. This treatment goal is noted as being important, since hypothermia itself may not be fatal above 25° C. core temperature. Fatalities at 25° C. or greater normally occur during rewarming.

The McEwan article notices that hypothermia causes several reactions within the body as it tries to protect itself and retain its heat, the most important of these being vaso constriction, which halts blood flow to the extremities in order to conserve heat in the critical core area of the body. Shivering is noted as maintaining peripheral vaso constriction, which minimizes the severity of vascular collapse during rewarming. Induction of vasodilation in hypothermia patients may precipitate rewarming shock and metabolic acidosis. This may occur where the periphery (legs and arms) are warmed before the core (heart and lungs) are warmed. Furthermore, the rapid shunting of cold blood from the extremities to the core as a direct result of vasodilation may cause the core temperature to drop. Prevention of vasodilation is the reason why it is imperative that the hypothermia victim's extremities not be rewarmed before the core. If vasodilation occurs, cold blood returning to the heart may be enough to put the patient into ventricular fibrillation. Again see, the McEwan article.

The McEwan article notes treatment for the different levels of hypothermia. According to McEwan, treatment for mild hypothermia includes keeping the head and neck covered. Stiff and Sixta note that treatment for mild hypothermia generally includes application of hot packs, water bottles, or warm campfire rocks wrapped in hot, wet towels to the groin, head, neck and sides of the chest. McEwan that treatment for moderate hypothermia includes keeping the head and neck covered, with mild heat applied to the head, neck, chest, armpits and groin of the hypothermia patient. For severe hypothermia, McEwan notes that treatment includes application of heat by skin to skin contact in the areas of the chest and neck with exhaled warm air or steam introduced near the patient's nose and mouth. Stiff and Sixta note that treatment for severe hypothermia will include application of hot packs to the neck, armpits, sides of chest and groin of the hypothermia victim, with the head kept covered.

Air-warmed and cooled devices to maintain normothermia during surgery are available and in wide use. However, as many as 10% of patients are hypothermic during surgery despite use of these devices. Both air-warmed and existing fluid-warmed devices (see FIG. 1) suffer from the same limitations. They do not contact an adequate amount of body surface to either maintain normothermia during surgery for parts of the body other than the brain, or to safely induce hypothermia during brain surgery or after head injury. The current lack of devices to effectively control patient temperature results in poor clinical outcomes in many cases.

The following patents relate to various apparatus for applying heat or cooling to a patient.

U.S. Pat. No. 2,093,834, issued Sep. 21, 1937 to Gaugler, discloses a refrigerating apparatus for use with a bed which generally includes a blanket having a plurality of ducts into which a cooling or heating medium is provided to either cool or heat a person lying in a bed.

U.S. Pat. No. 2,110,022, issued Mar. 1, 1938 to Kliesrath, discloses a bed cover in which a heating or cooling medium is circulated.

U.S. Pat. No. 2,512,559, issued Jun. 20, 1950 to Williams, discloses a pad or blanket or the like which is associated with a heat transfer unit for heating or cooling a person lying in a bed.

U.S. Pat. No. 2,938,356, issued May 31, 1960 to McMahon, discloses bedding in the form of sheets, blankets or mattresses, or a flying suit, which may be utilized to heat or cool an individual using the bedding or flying suit. The bedding or flying suit may be described as a flexible supporting material of low conductivity which has embedded in it two types of segments each type of which is at least semi-conductive. A direct current is passed through this material in such a manner that heat will be absorbed or given off at junctions depending upon the direction of the current.

U.S. Pat. No. 2,991,627, issued Jul. 11, 1961 to Suits, discloses a cooling and heating blanket which may be placed in close proximity to a human body. The cooling and heating blanket utilizes a plurality of Peltier junctions through which direct electrical current is passed to obtain heating or cooling. This Peltier effect may be enhanced by circulating air through the blanket in a flexible tube.

U.S. Pat. No. 3,112,792, issued Dec. 3, 1963 to Coleman, et al, discloses a personal thermal device which is essentially a full body suit through which a heat transfer fluid is circulated throughout. The design of the '792 patent does not allow differential heating and cooling capability or exposed body parts for access for medical procedures.

U.S. Pat. No. 3,154,926, issued Nov. 3, 1964 to Hirschhorn, discloses, discloses a cooling blanket in which cold fluid is pumped through a plurality of rigid metal tubes.

U.S. Pat. No. 3,211,216, issued Oct. 12, 1965, to Coleman, et al, is a divisional of earlier described patent U.S. Pat. No. 3,112,792.

U.S. Pat. No. 4,094,357, issued Jun. 13, 1978, to Sgroi, discloses a heat transfer blanket having a plurality of flexible heat pipe sandwich between the outer most layers of the blanket.

U.S. Pat. No. 4,017,921, issued Apr. 19, 1977, to Hernandez, discloses a cooling blanket which utilizes a plurality of elongated chambers defined normally by a plurality of elongated joints between the blanket lamina, wherein the chambers are adapted for receiving ice.

U.S. Pat. No. 4,114,620, issued Sep. 19, 1978, to Moore, et al, discloses a patient treatment pad for hot or cold use which utilizes a pair of laminated plastic film panels defining a passage there between for circulating hot or cold water.

U.S. Pat. No. 4,118,946, issued Oct. 10, 1978, to Tubin, discloses a flexible sheet or garment to be worn on or around the human body, or body member for cooling, which flexible sheet or garment a viscous liquid heat transfer media in a first fluid path and a pressurized gas in a second fluid path to transfer heat away from the body. The '946 device, however, is to be worn in situations of high external temperature and is not suited for medical applications where very precise control of the temperature of an injured or ill person who cannot auto regulate their own temperature is desired. Also, the '946 devise's rectangular shape that does not conform to the body.

U.S. Pat. No. 4,132,262, issued Jan. 2, 1979, to Wibell, discloses a heating and cooling blanket with heating means including a plurality of flexible elements positioned within the blanket for being electrically energized for supplying heat to the blanket, and cooling means including plurality of flexible fluid carrying conduits positioned within the blanket to which a heat transfer fluid can flow, such that the blanket may be retained below room temperature. These heating and cooling elements are provided in such a manner as to provide a thermal blanket having respective independently controllable zones, such that the zones may either concurrently heat and cool the user of the blanket. The '262 invention discloses zones which may be independently heated and cooled. However, the zones of the '262 device are rectangular zones in a rectangular blanket which neither conforms to the body nor provides access to the body for surgery or medical care.

U.S. Pat. No. 4,149,541, issued Apr. 17, 1979, to Gammons, et al, discloses a fluid circulating pad with interconnecting internal passages for circulating a hot or cold liquid for treating a patient.

U.S. Pat. No. 4,660,388, issued Apr. 28, 1987, to Greene, Jr., discloses a cooling cover comprising a plurality of small air jets through which air is directed onto the body of a user of the cooling cover.

U.S. Pat. No. 4,662,433, issued May 5, 1987, to Cahn, et al, discloses a cooling blanket which utilizes a stable circulating foam as the cooling medium.

U.S. Pat. No. 4,859,250, issued Aug. 22, 1989, to Buist, discloses a thermal electric heat pump or power source device which is provided with P-type and N-type elements made of either thin films or thick films for use on flexible or nonflexible substrates such as thermals, blankets or therapeutic devices for heating or cooling.

U.S. Pat. No. 5,014,695, issued May 14, 1991, to Benak, et al, discloses a cooling/warming jacket pad for the containment of physiological organs such as hearts and kidneys during medical procedures. The jacket of the '695 patent, however, is designed to wrap around an organ inside the body.

U.S. Pat. No. 5,125,238, issued Jun. 30, 1992, to Ragan, et al, discloses a disposable patient heating or cooling blanket. The patient is bathed and conditioned air through a multiplicity of orifices in the bottom layers of the blanket and the size and location of the orifices are such that sufficient pressure exists within the blanket to prevent crimping blockage and to insure a uniform flow of air through the orifices throughout the blanket area.

U.S. Pat. No. 5,165,127, issued Nov. 24, 1992, to Nicholson, discloses a heating and cooling blanket apparatus which utilizes a circulating heat transfer fluid.

U.S. Pat. No. 5,265,599, issued Nov. 30, 1993, to Stephenson et al, discloses a patient temperature control blanket with controlled air distribution. The blanket is provided with a plurality of orifices through which controlled pressurized air is introduced upon the patient's body to regulate patient body temperature.

U.S. Pat. No. 5,392,847, issued Feb. 28, 1995, to Stephenson, discloses a thermal medical blanket which distributes heated or cooling air upon the patient.

In 1992, one of the inventors utilized a modified non-commercial embodiment of the RotoRest bed (Kinetic Concepts, Inc.) in an hypothermia study. This bed had been equipped with cooling panels for wrapping the abdomen and chest. Unfortunately, this bed does not have the capability of warming and cooling different body surfaces at the same time, the cooling apparatus cannot be used independently of the bed, and the bed cannot be used in the operating room or post operative room because of limitations imposed on patient care by the RotoRest bed.

However, in spite of these advancements in the prior art, none of these prior art references disclose or suggest, an apparatus for selective rewarming of a hypothermia patient to rewarm various body parts at different rates and at different temperatures to minimize the occurrence of vasodilation. Additionally, none of these prior art references disclose a suit which wraps the torso and legs leaving the arms, buttocks, perineum and head exposed. Furthermore, none of the prior art references disclose panels which may be opened to gain access to the chest, abdomen, legs or backs to expose a surgical field or to provide access to these areas for necessary medical care.

For example, in the situation of a patient suffering from hypothermia or in whom hypothermia has been deliberately induced, exposure of the arms is necessary as they are the primary site for insertion of necessary intravenous lines. Exposure of the head is necessary to maintain control of the airway. The ability to gain ready access to the chest, back and abdomen (the core) is necessary should cardiopulmonary resuscitation be needed, to auscultate heart and breath sounds, to auscultate abdominal sounds or to provide exposure for surgeries of the chest, back or abdomen. Exposure of the legs is necessary for hygiene or for surgery of the legs. The perineum is always exposed in order to provide access at all time to the urinary tract and also because of the significant hygiene issues associated with these sites where body wastes are eliminated. Firm contact of the blanket to the torso and legs, however, is necessary to control temperature whether inducing hypothermia, maintaining hypothermia or rewarming. In a medical setting however, ready access to the torso and legs and exposure of head arms and perineum is required. None of the devises of the prior art meets these needs.

Thus, there is still a need in the art for apparatus for selective heating and cooling of various body parts of a human suffering from hypothermia so that various body parts can be heated and cooled at different rates and at different temperatures.

There is still another need in the art for an apparatus for heating and cooling of a patient in which the maximal body surface is in contact with the cooling/heating surface, which will also provide for easy access to the patient's body for either surgery or routine patient care, while the patient is being heated and/or cooled.

These and other needs in the art will become apparent to those of skill in the art upon review of this specification, including its drawings and claims.

SUMMARY OF THE INVENTION

It is an object of the present invention to provide for an apparatus for the selective heating and cooling of a patient so that various body parts can be heated and cooled at different rates and at different temperatures.

It is another object of the present invention to provide for an apparatus for the heating and cooling of a patient which also allows for easy access to various body parts of the patient during such heating and cooling.

These and other objects of the present invention will become apparent to those of skill in the art upon review of this specification, including its drawings and claims.

In one embodiment of the present application there is provided an apparatus for providing heating and cooling to a human body having a torso, legs, axillae, and ilia, with an axillary line defined as running between the axillae, and with an iliac line defined as running between the ilia. The apparatus includes at least one torso panel, suitable for wrapping the torso, defining cradles for receiving the axillae, where at least a portion of the torso panel extends above the axillary line and at least one fluid communication system providing fluid circulation within the torso panel.

In another embodiment of the present application there is provided an apparatus for providing heating and cooling to a human body having a torso, legs, axillae, and ilia, with an axillary line defined as running between the axillae, and with an iliac line defined as running between the ilia. The apparatus includes at least one torso panel suitable for wrapping the torso, where the torso panel defines curvilinear saddles for receiving the ilia, where at least a portion of the torso panel extends below the iliac line and a fluid communication system in fluid communication providing fluid circulation within the torso panel.

In even another embodiment of the present application there is provided an apparatus for providing heating and cooling to a human body having a torso, legs, axillae, and ilia, with an axillary line defined as running between the axillae, and with an iliac line defined as running between the ilia. The apparatus includes a first torso panel suitable for wrapping the torso, wherein the first torso panel defines cradles for receiving the axillae, where at least a portion of the first torso panel extends above the axillary line, a second torso panel suitable for wrapping the torso, wherein the second torso panel defines curvilinear saddles for receiving the ilia, where at least a portion of the second torso panel extends below the iliac line, and at least one fluid communication system in fluid communication with and providing fluid circulation within the first and second torso panels.

In even still another embodiment of the present application there is provided an apparatus for providing heating and cooling to a human body having a torso, the apparatus includes a panel having left and right outer edges, and positioned therebetween a left portion, a middle portion, and right portion, with both the left portion and the right portion further have a top and bottom portions, with the top and bottom portions of the left portion defining a left split running from the left outer edge to a left split point on the panel which defines a left edge of the middle portion, with the top and bottom portions of the right portion defining a right split running from the right outer edge to a right split point on the panel which defines a right edge of the middle portion, with the middle portion suitable for receiving at least a portion of the torso, and the upper and lower portions suitable for wrapping at least a portion of the torso.

In even still another embodiment of the present application there is provided an apparatus for providing heating and cooling to a human body having a leg comprising an upper leg, a knee, and a lower leg, the apparatus includes a panel including left and right outer edges, and positioned therebetween a left portion, a middle portion, and right portion, with both the left portion and the right portion further including upper leg and lower leg portions suitable from wrapping the upper leg and lower leg respectively, with the upper leg and lower leg portions of the left portion defining a knee opening running from the left outer edge to a left split point on the panel which defines a left edge of the middle portion, with the upper leg lower leg portions of the right portion defining a right split running from the right outer edge to a right split point on the panel which defines a right edge of the middle portion, wherein the middle portion is suitable for receiving at least a portion of the leg.

DETAILED DESCRIPTION OF THE INVENTION

Figure 1:
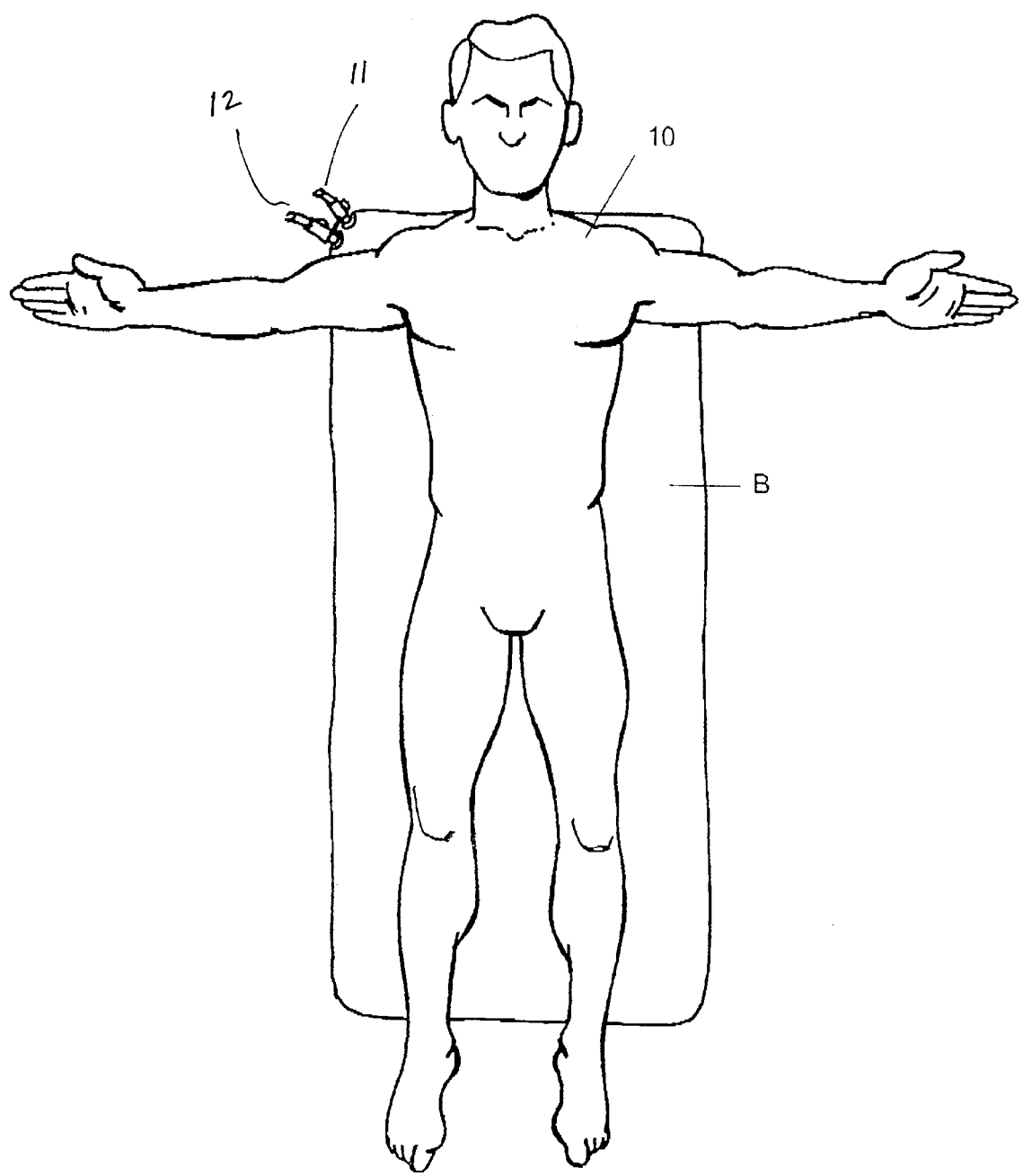
FIG. 1 is an illustration of patient 10 shown positioned on a prior art blanket B.

Prior to discussion of the details of the present invention, reference will first be made to a commonly used prior art blanket. Referring first to FIG. 1, there is shown an illustration of patient 10 shown positioned on a prior art blanket B. The configuration of a prior art blanket shown generally in FIG. 1 is currently the only configuration commercially available to provide whole body surface cooling. A heat transfer fluid is circulated into and out of blanket B utilizing tubing 11 and 12 respectively. Notice how blanket B generally makes contact with only a limited portion of the skin surface of patient 10, generally the back or front body portion upon which patient 10 is resting. In the supine position, prior art blanket B does not contact the contour of the body. When blanket B contacts the posterior surface of patient 10, it only contacts the scapulae, the buttocks, and the posterior surface of the lower legs. If anterior, prior art blanket B only contacts the area of the pectoralis muscles or breasts on the chest, the anterior aspect of the abdomen, and the anterior aspect of the upper leg and knee. In addition, in the operating room where a patient is on his side, prior art blanket 10 would only contact the side of the patient. Furthermore, due to its rectangular shape, prior art blanket 10 cannot wrap the legs or the trunk, thus leaving the majority of the body surface uncontacted by the blanket. In any of the above situations, the heat transfer area could be improved.

Figure 2:
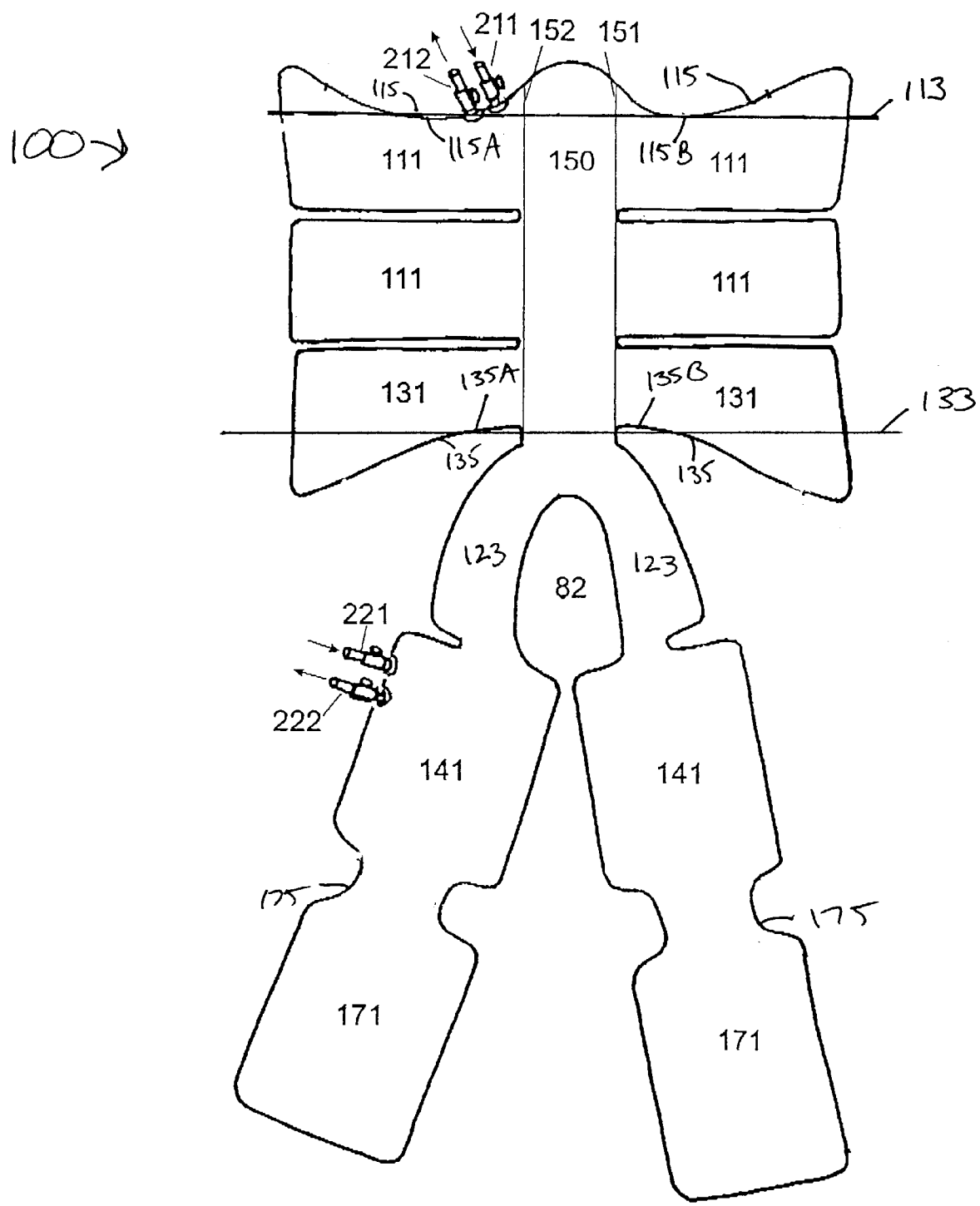
FIG. 2 is an illustration of one embodiment of heating and cooling blanket 100 of the present invention, with main panel 150, chest panels 111, abdomen panel 131 upper leg panel 141, lower leg panel 171, cutout portion 175 between panels 141 and 171, projections 115 extending above axillary line 113 and projections 135 extending below iliac line 133.

The present invention will now be described by reference to FIGS. 2–11. Referring first to FIG. 2 there is shown one embodiment of heating and cooling blanket 100 of the present invention, main panel 150, upper leg panel 141 and lower leg panel 171 with connecting area 123. Heating and cooling blanket 100 provides for the wrapping of the chest, abdomen, and upper and lower legs using various panels 111, 131, 141 and 171, respectively. These various panels may be opened for access during surgery, medical procedures or hygiene.

Figure 8:
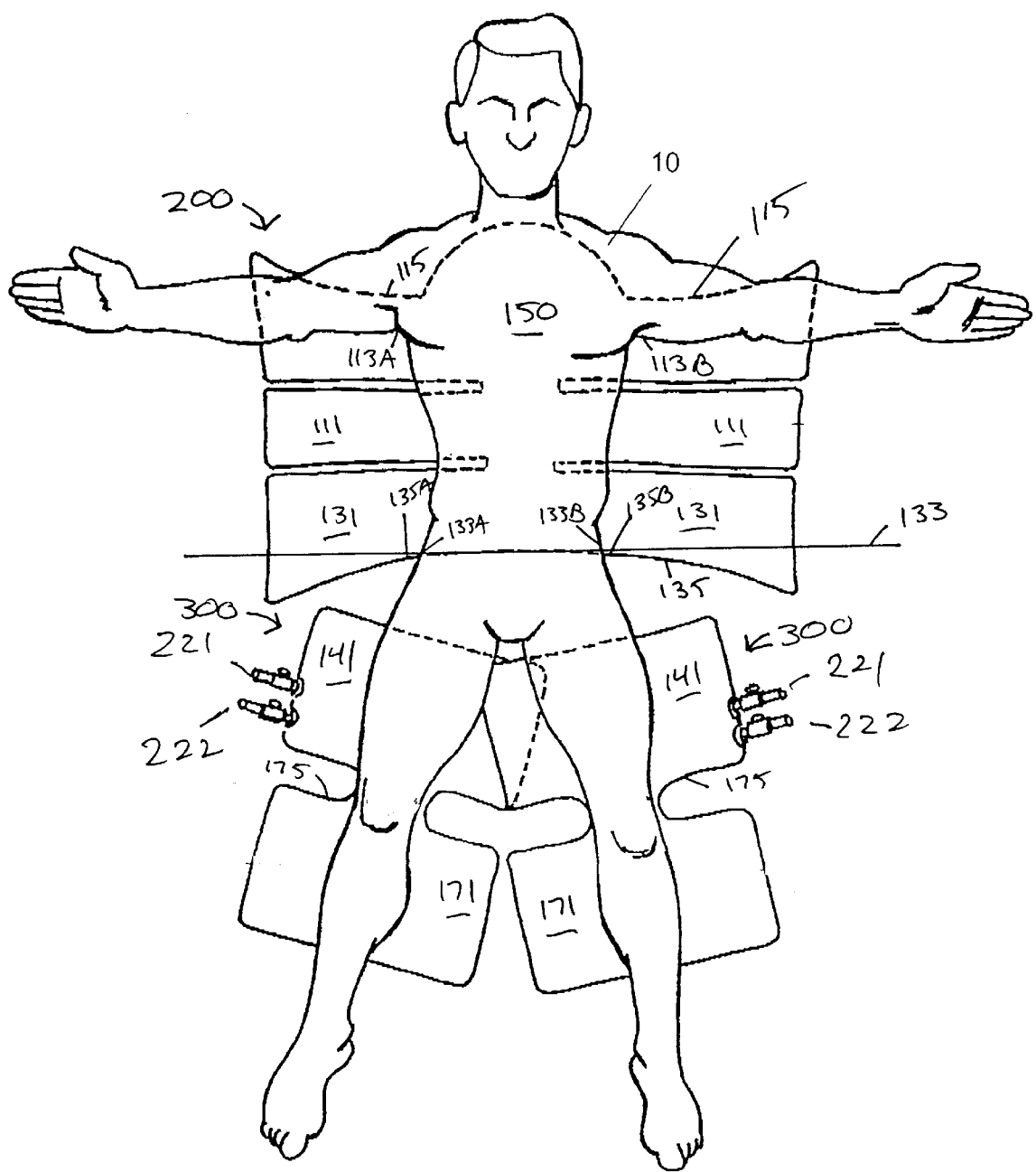
FIG. 8 is an illustration of patient 10 positioned on heating and cooling blanket 200 and on heating and cooling blankets 300 of the present invention, where leg wraps 300 are independent of each other and of torso wrap 200.

Referring now to FIG. 8 there is shown another embodiment of heating and cooling blankets 200 and 300 of the present invention. Cooling blanket 200 contains chest panels 111 and abdomen panel 131 connected to main panel 150 and provides for the wrapping of the chest and abdomen. Cooling blanket 300 contains lower leg panel 171 connected via knee opening 175 to upper leg panel 141 and provides for the wrapping of a leg with no contact or pressure point of the blanket on the knee. Knee opening 175 may be of any suitable shape. Non-limiting examples of suitable shapes for knee opening 175 include circular, oval, rectangular, square, any n-sided regular or irregular geometric shape, or a combination thereof.

Figure 3:
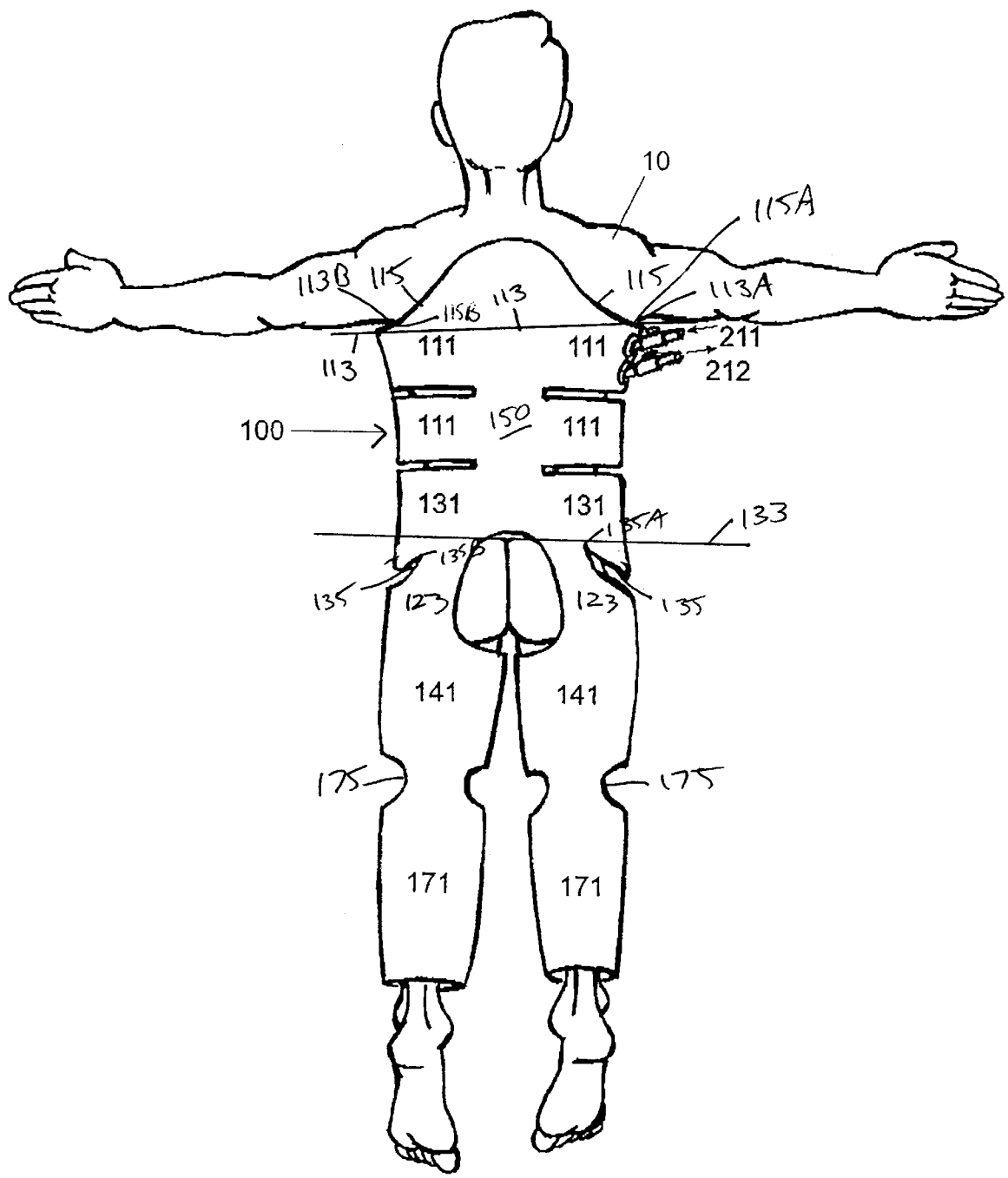
FIG. 3 is a an illustration showing back view of patient 10 positioned on heating and cooling blanket 100 with main panel 150, chest panels 111, abdomen panels 131, upper leg panels 141 and lower leg panels 171 wrapping respectively, the chest, abdomen, and upper and lower legs with connecting area 123 and cutout portion 175.

Referring now additionally to FIG. 3 there is shown an illustration showing back view of patient 10 positioned on heating and cooling blanket 100 with chest panels 111, abdomen panels 131, upper leg panels 141 and lower leg panels 171 wrapping respectively, the chest, abdomen, and upper and lower legs with connecting area 123 and curvilinear portions 115 and 175. In this view, all panels 111, 131, 141 and 171 of blanket 100 are closed thereby providing maximum coverage of the body surface area during such time when surgical or medical access is not required for patient care.

Figure 4:
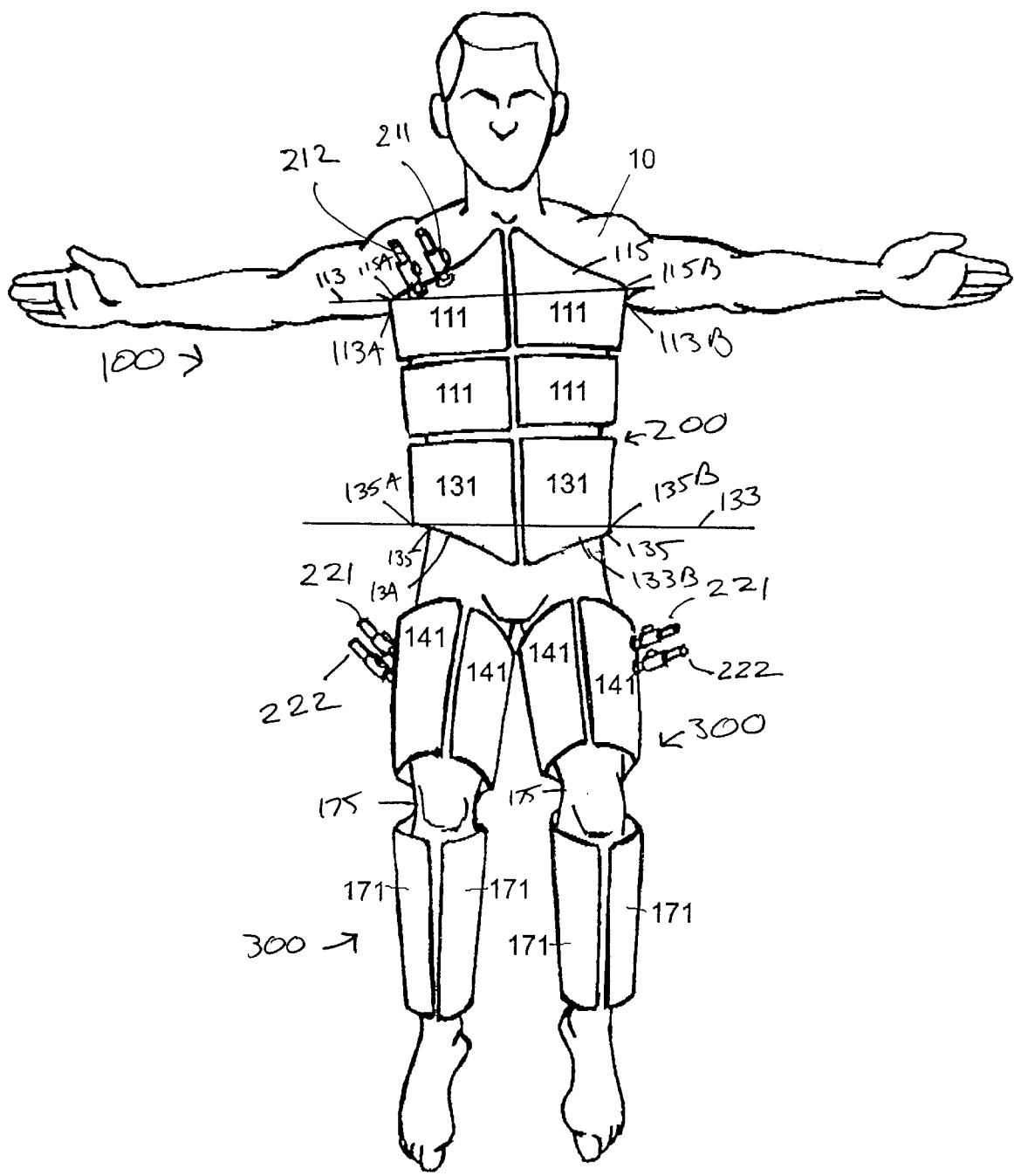
FIG. 4 is an illustration showing front view of blanket 100 or in another embodiment front. view of blankets 200 and 300 (illustrated in FIG. 8) with patient 10 positioned on blankets 100 and 200 with chest panels 111, abdomen panels 131, upper leg panels 141 and lower leg panels 171 with all panels closed.

Referring now to FIG. 4 there is shown an illustration showing a front view of blanket 100 or a front view of blankets 200 and 300 (illustrated in FIG. 8) with patient 10 positioned on either single blanket 100 or on separate blankets 200 and 300 with chest panels 111, abdomen panels 131, upper leg panels 141 and lower leg panels 171. In this view, all panels 111, 131, 141 and 171 of blanket 100 or of blankets 200 and 300 are closed thereby providing maximum coverage of the body surface area during such time when surgical or medical access is not required for patient care. Note that curvilinear portion 175 allows closure of panels 141 and 171 with no contact or pressure point of the blanket of the present invention on the knee or knees.

Figure 5:
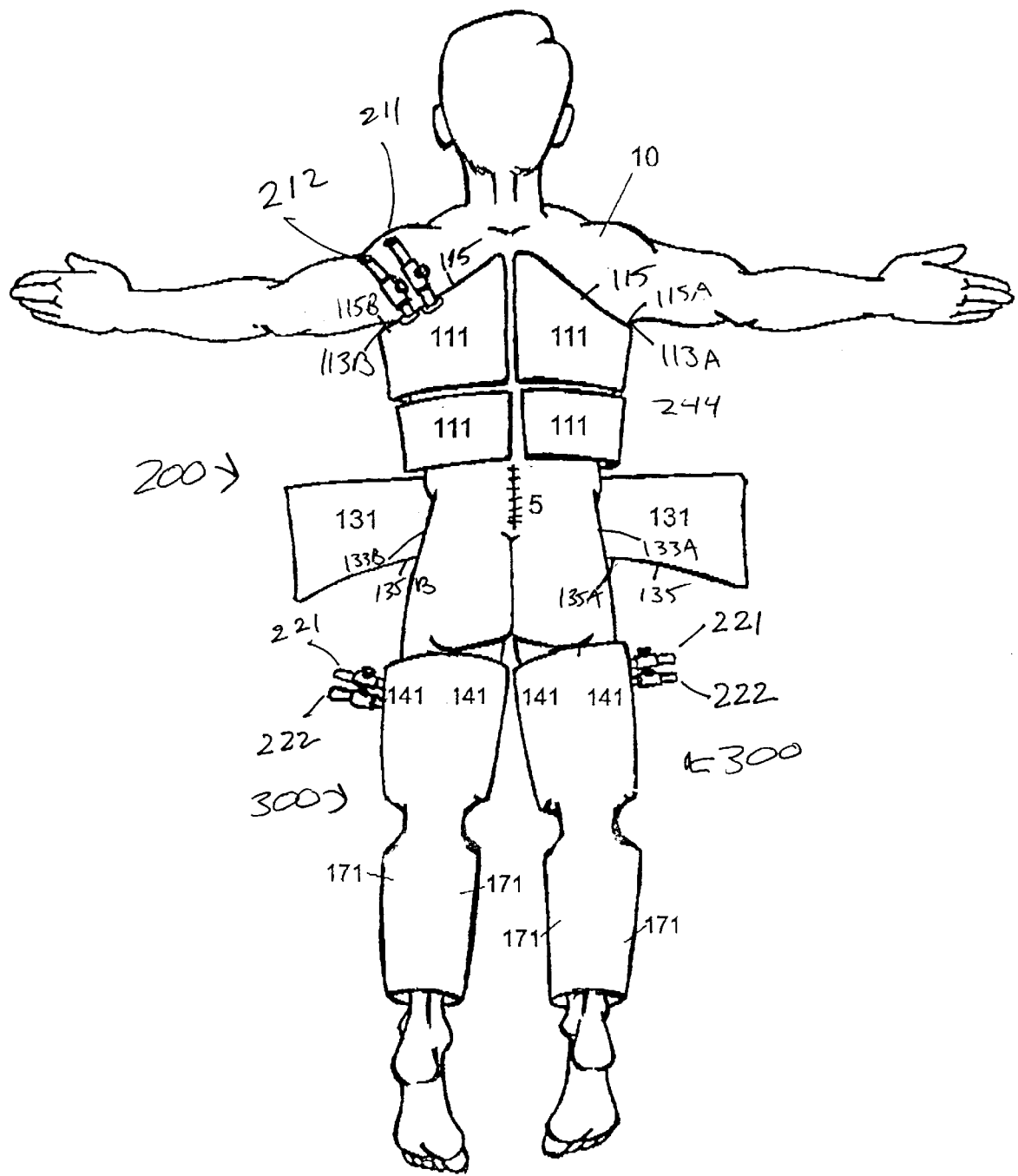
FIG. 5 is an illustration showing patient 10 in the prone position on heating and cooling blankets 200 and 300 with abdomen panels 131 opened to allow for surgical access to patient's back 5. Blanket 200 is reversed so that main panel 150 is anterior to patient 10 permitting abdomen panel 131 to be open for surgical access to back with incision illustrated.

Referring now to FIG. 5 there is shown an illustration of patient 10 in the prone position on heating and cooling blankets 200 and 300 with abdomen panels 131 opened to allow for surgical access to patient's back 5. Blanket 200 is reversed and a surgical incision is illustrated. Receiving area or main panel 150 (illustrated in FIG. 8) receives the anterior of patient 10 so that panels 111 and 131 of blanket 200 open on the posterior surface of patient 10. Placing patient 10 on blanket 200 in this way provides for surgical exposure of the back when patient 10 is in the prone position while providing maximal contact of patient 10 body surface with heating/cooling blanket 200 during surgery. Note that in FIG. 5, blankets 300 are placed such that panels 141 and 171 open anteriorly thereby preventing pressure points on the knee or knees.

Figure 6:
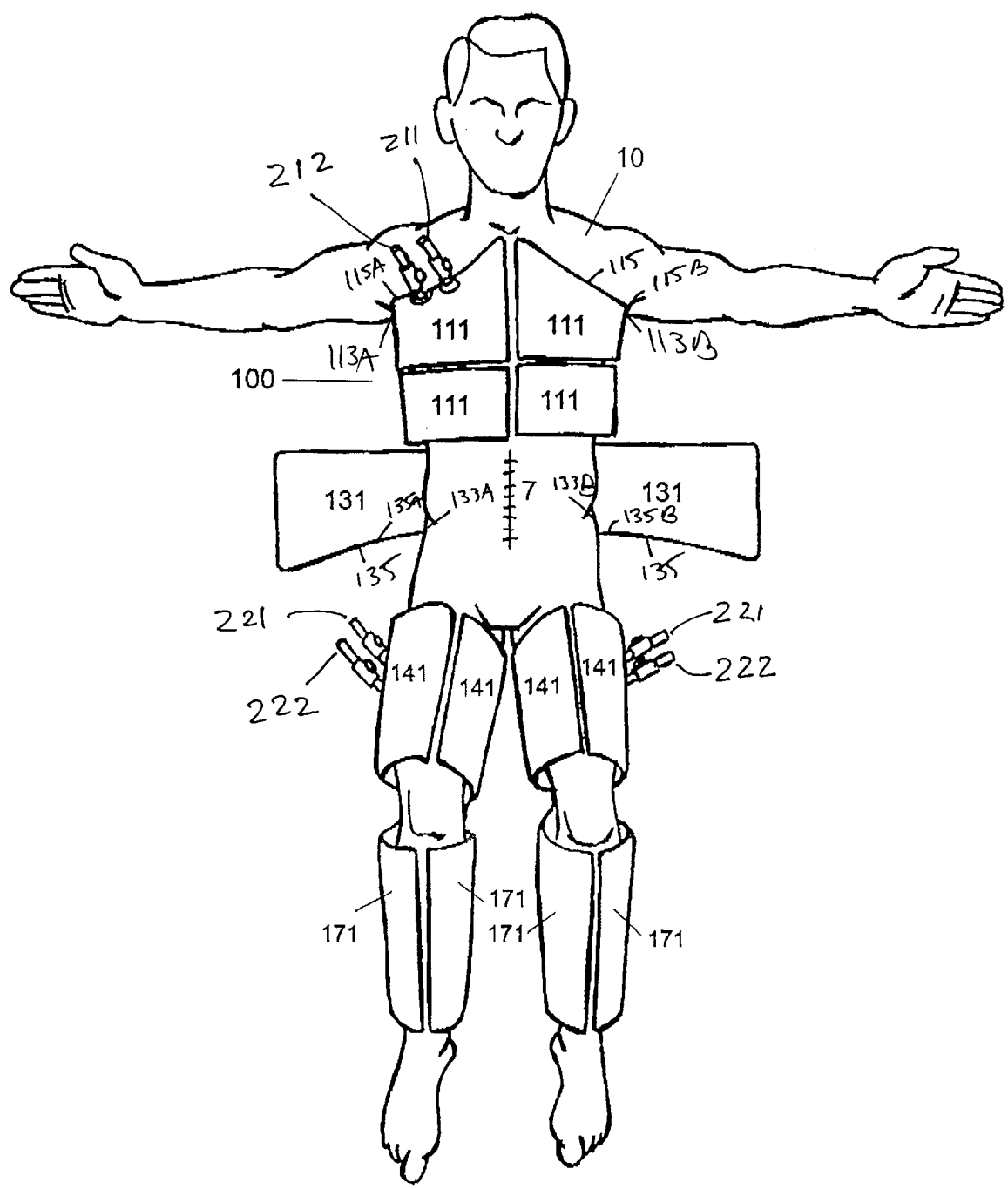
FIG. 6 is an illustration showing patient 10 positioned on heating and cooling blankets 100 or 200 and 300 with abdomen panels 131 opened to allow for surgical access to patient's abdomen 7. Connecting panel 123 of blanket 100 and main panel of blankets 100 and 200 are not visible in this orientation.

Referring now to FIG. 6 there is shown an illustration of patient 10 positioned on single heating and cooling blanket 100 or on separate heating and cooling blankets 200 and 300 with abdomen panels 131 opened to allow for surgical access to patient's abdomen 7. Placing patient 10 on blanket 100 or on blankets 200 and 300 in this position provides access to the abdomen 7, with representative surgical incision, by opening only panel 131. Placing patient 10 on blanket 100 or on blankets 200 and 300 in this way provides for surgical exposure to abdomen 7 when patient 10 is in the supine position, while providing maximal contact of patient 10 body surface with heating/cooling blanket 100 or blankets 200 and/or 300 during surgery.

Figure 7:
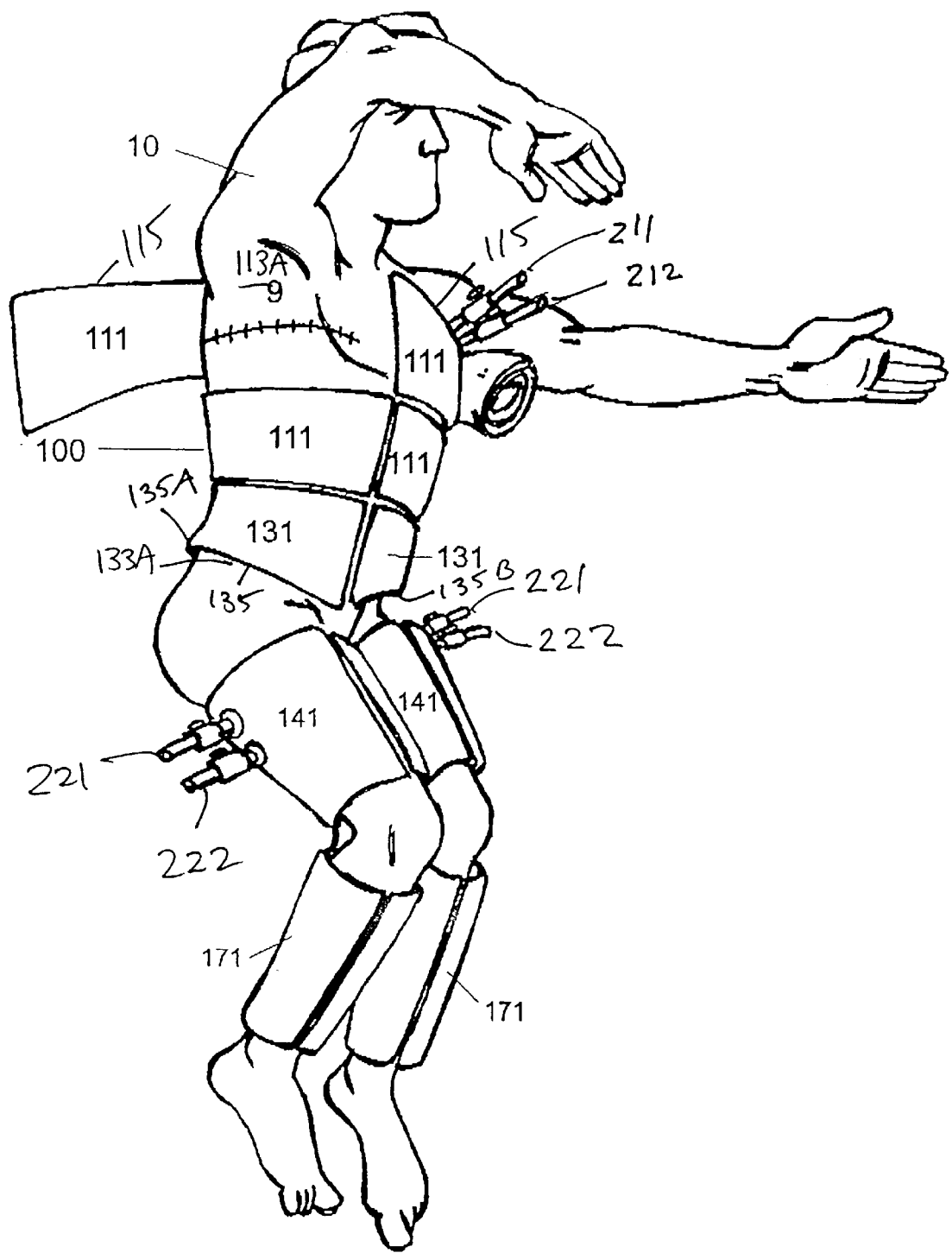
FIG. 7 is an illustration showing patient 10 in a lateral position on heating and cooling blankets 100 or 200 and 300 with with chest panel 111 open to expose the upper right portion of patient's chest 9. Main panel 150 (not seen) permits chest panel 111 to be opened to near the spine of patient 10 permitting surgical access.

Referring now to FIG. 7 there is shown an illustration of patient 10 in a lateral position on heating and cooling blanket 100 or on blankets 200 and 300 with chest panel 111 open to expose the upper right portion of patient's chest 9. Preferably, central panel 150 as shown in FIGS. 2 and 8, must be narrow enough that the thoracic incision may be carried well posteriorly. Unique to the heating and cooling blankets of the present invention, maximum contact between the blankets and body surface of patient 10 is effectuated even when patient 10 is in lateral position. Prior art blanket B would only contact lateral aspect of the dependant portion of the body with patient 10 in the same position.

Referring now to FIG. 8 there is shown an illustration of patient 10 positioned on heating and cooling blanket 200 and on heating and cooling blankets 300 of the present invention with all panels open.

Figure 9:
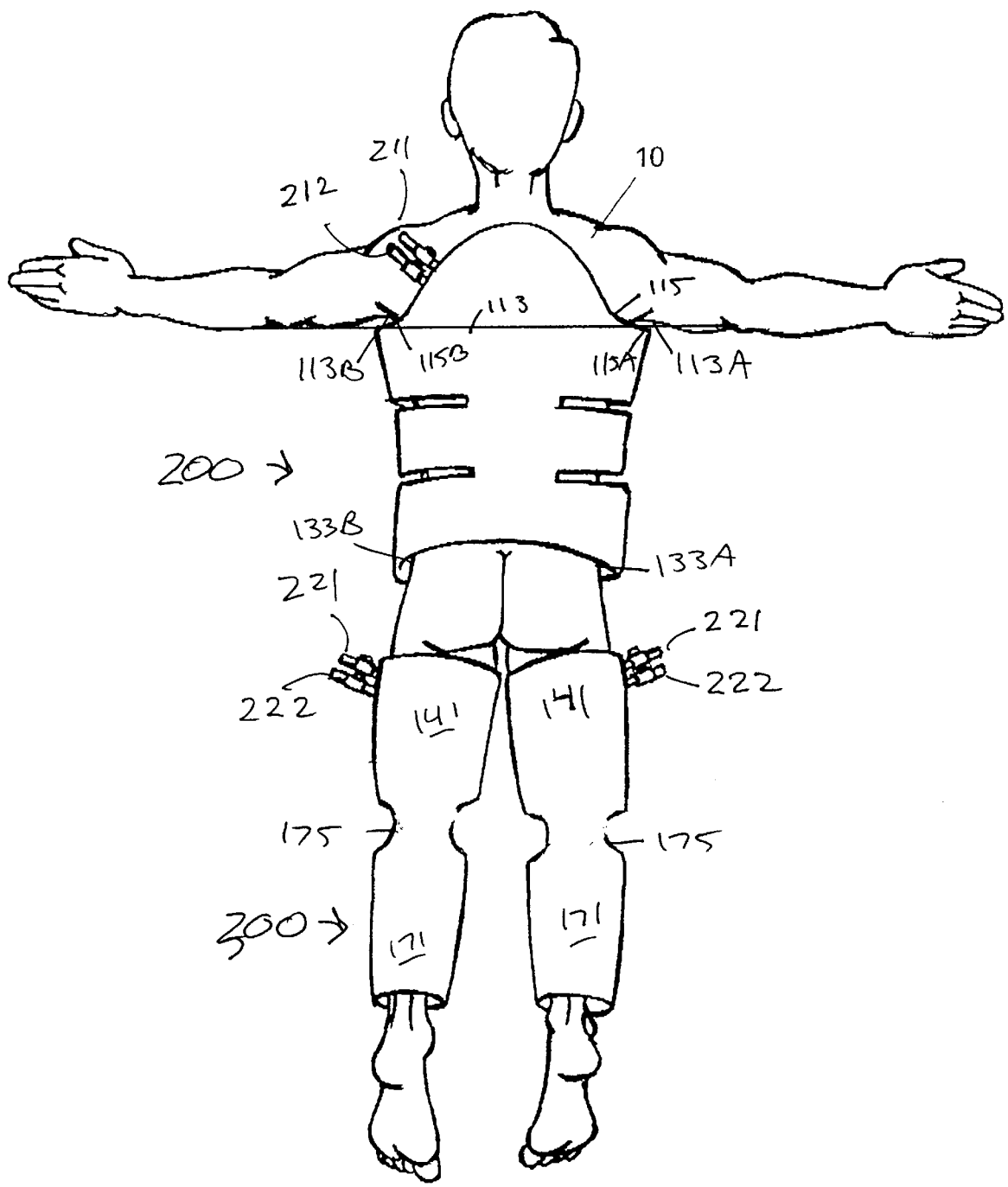
FIG. 9 is an illustration showing a back view of patient 10 positioned on the heating and cooling blanket 200 and blankets 300 of FIG. 8. The anterior view of FIG. 9 is the same as shown in FIG. 4.

Referring now to FIG. 9 there is shown an illustration of patient 10 positioned on the heating and cooling blanket 200 and blankets 300 of FIG. 8. The anterior view of FIG. 9 is the same as shown in FIG. 4.

Figure 10:
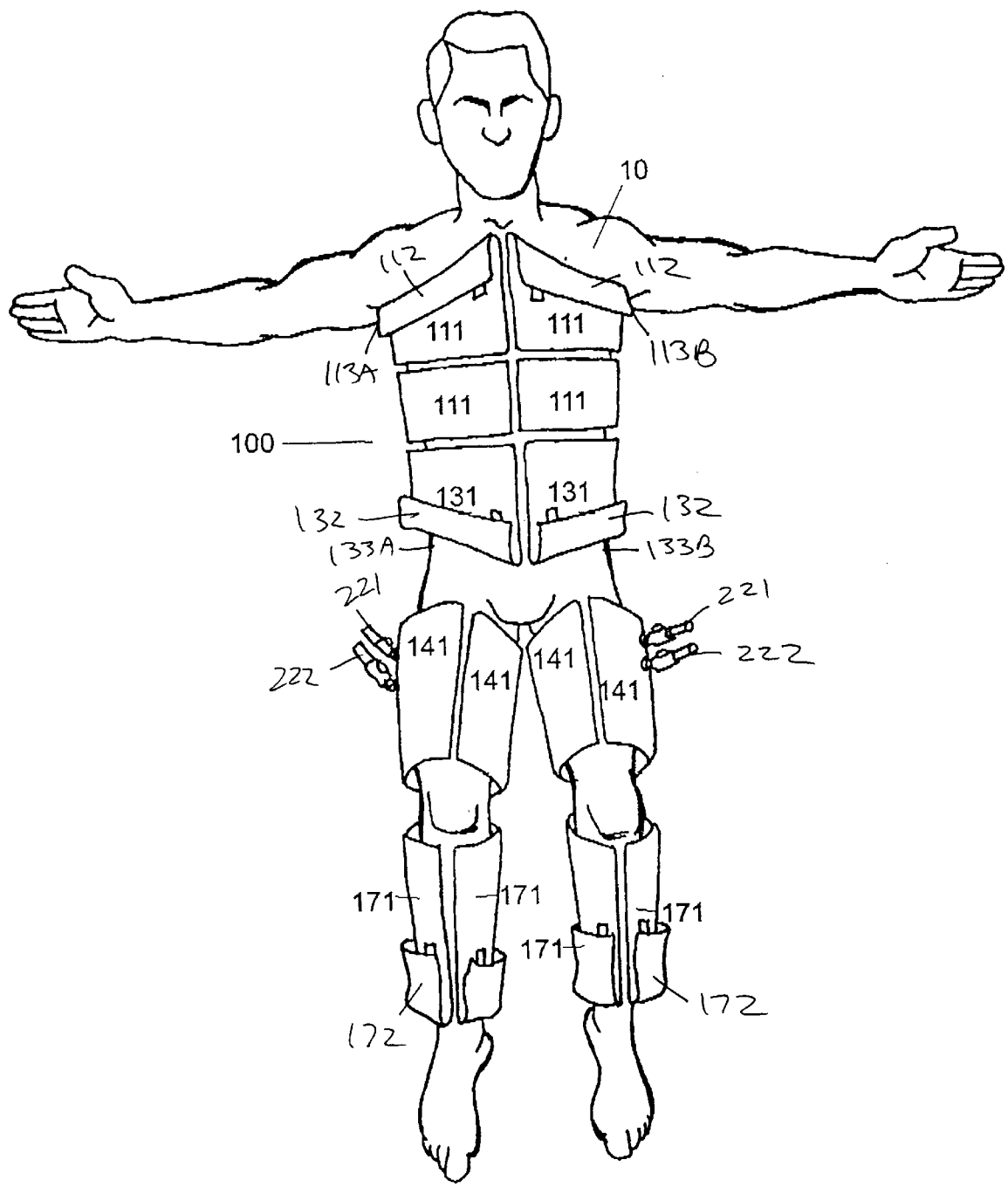
FIG. 10 is an illustration showing the front view of patient 10 positioned on heating and cooling blanket 100 or on blankets 200 and 300 with chest panels 111 having extensions 112, abdomen panels 131 having extensions 132, upper leg panels 141 and lower leg panels 171 having extensions 172 wrapping respectively, the chest, abdomen, and upper and lower legs.

Referring now to FIG. 10 is an illustration showing the front view of patient 10 positioned on heating and cooling blanket 100 or on blankets 200 and 300 with chest panels 111, having extensions 112, abdomen panels 131 having extensions 132, upper leg panels 141 and lower leg panels 171 having extensions 172 wrapping respectively, the chest, abdomen, and upper and lower legs. Extensions 172 could be positioned on the superior portion of panel 141 or on the inferior portion of 171.

Figure 11:
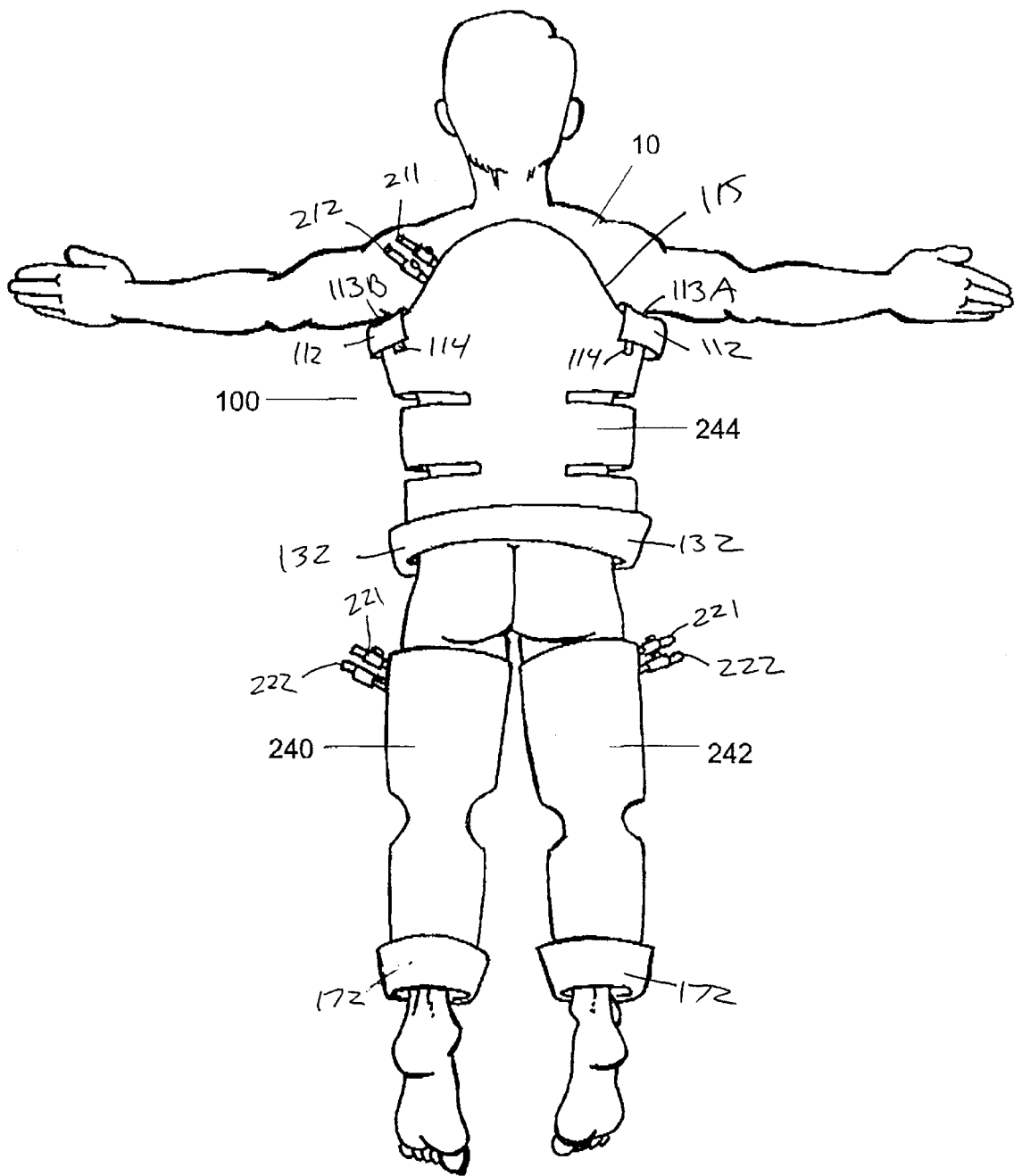
FIG. 11 is an illustration showing the back view of patient 10 positioned on heating and cooling blankets 200 and 300 with chest panels 111, having extensions 112, abdomen panels 131 having extensions 132, upper leg panels 141 and lower leg panels 171 having extensions 172 wrapping respectively, the chest, abdomen, and upper and lower legs.

Referring now to FIG. 11 there is shown an illustration showing the back view of patient 10 positioned on heating and cooling blankets 200 and 300 with chest panels 111, having extensions 112, abdomen panels 131 having extensions 132, upper leg panels 141 and lower leg panels 171 having extensions 172 wrapping respectively, the chest, abdomen, and upper and lower legs. Extensions 172 could be positioned on the superior portion of panel 141 or on the inferior portion of 171.

Optional extension panels 112, 132, and 172 permit one size of blanket 100 or blankets 200 and 300 to fit a wider range of body sizes. For example, as shown in FIGS. 10 and 11, for smaller persons, panels 112, 132, and 172 are folded or rolled upwards being secured in place by their own weight or optionally by fasteners 114, 134, and 174 respectively. For larger individuals, any number of extension panels 112, 132 or 172 may be individually unfolded or unrolled to provide coverage to a larger portion of the person's body. As above, panel extensions 112, 132, and 172 may also be folded or rolled to provide access for surgery, medical procedures or hygiene.

Panel extensions 112, 132, and 172 may be secured in place by their own weight, with adhesive tape, or by any suitable fastener 114, 134 and 174 including snaps, buttons, hooks, zippers, and hook and loop type systems a commercially available example which includes VELCRO.

Panel extensions 112, 132, 172 may be of any shape suitable to provide the desired coverage. It is understood that extensions 112, 132 and 172 may be tapered or otherwise contoured to conform to the shape of the body.

Notice that the blankets of the present invention provide full access to the head and neck, the arms, the feet, and the perineum. Although not necessary, it is desirable that heating and cooling blankets 100, 200 and 300 be reversible, that is, that patient 10 may be placed on either surface of blankets 100, 200 or 300.

Referring to FIGS. 2 and FIG. 8, main panel 150 is provided so that in the lateral position during surgery heating and cooling blanket 100 or 200 may optionally be used with one or more panels opened, providing full access to the thorax and the flanks for surgery. Main panel 150 generally extends from the neck to the buttocks and is bounded by fold lines 151 and 152, with the distance between fold lines in the range of about 2 to about 12 inches, preferably in the range of about 4 to about 6 inches.

Referring now additionally to FIGS. 4, 6 and 7, the purpose of the central or main panel 150 is also to provide an attachment locations for panels 111 and panels 131 such that the slight gap between the panels allows panels 111 or 131 to be independently opened without obstructing surgical access to the lateral portion of the chest or of the flank. This feature allows select surgical access to the chest and/or the abdomen while patient 10 in the lateral, prone and supine positions while still providing for maximum coverage of patient 10.

It is generally desirable to provide for spacing between chest panels 111 and abdomen panels 131, to allow for access to the abdomen during laparotomy. While in the embodiment as shown, only the upper edge of chest panels 111 are tapered, this may be accomplished by providing one or both of the panels 111 and 131 with a slight taper or angle to provide for spacing between panels 111 and 131.

Preferably, to provide coverage to a larger surface area of the body, panel 111 may contain one or more axillary curvilinear portions 115, as shown in the figures such that when panel 111 encircles the body, the one or more curvilinear portions 115 define axillary cradles 115A and 115B positioned under and adjacent to axillae 113A and 113B such that at least a portion of panel 111 extends above line 113 drawn between the axillae 113A and 113B. In addition, panel 131 may contain one or more ilia curvilinear portions 135 such that when panel 131 encircles the body, the one or more curvilinear portions 135 define ilia saddles 135A and 135B positioned above and adjacent to iliac crest 133A and 133B such that at least a portion of panel 131 extends below line 133 drawn between the iliac crest 133A and 133B. Although the cradles 115A and 115B and saddles 135A and 135B are generally defined as curvilinear in shape, it is understood that they may be any suitable shape or cut out portion to receive the axillae and ilia respectively. Non-limiting examples of suitable shapes for cradles 115A and 115B and for saddles 135A and 135B included square, rectangular, oval, any regular or irregular geometric shape, or a combination thereof.

As shown in FIG. 2, perineum opening 82 of blanket 100 provides both anterior and posterior access at the perineum for hygiene and for catheter egress. Alternatively, heating and cooling blanket 100 of the present invention may be provided with a disposable surface at the perineum to prevent soiling of blanket 100.

Heating and cooling apparati 100, 200 and 300 of the present invention may be provided with a heat transfer fluid to allow for heating or cooling. Generally, a heat transfer fluid, most commonly water, is circulated through heating and cooling blanket 100, 200 or 300 which is generally provided with internal passages, tubing, channels or the like. This heat transfer fluid is provided at a desired temperature, and is circulated at a desired rate to provide the desired heating or cooling to patient 10.

The entire heating and cooling blanket 100, 200 or 300 may consist of a single fluid communication zone. Such an arrangement would provide essentially a single temperature throughout, with minor temperature deviations depending upon the fluid flow patterns.

Alternatively, heating and cooling blanket 100 and blankets 200 and 300 could be provided with two or more fluid communication zones which may be independently heated and/or cooled as desired. For example, fluid to main panel 150 would be provided through connectors 211 and 212 for this application. Fluid to leg panels 141 and 171 would be provided through connectors 221 and 222 in this application. For example, panels 111 with optional extension 112, 131 with optional extension 132, 141 and 171 with optional extension 172 could be provided with independent fluid circulation and independently heated and/or cooled as desired. As another example, for those surgical procedures requiring the temperature of the upper body to be independently controlled from that of the lower body, upper body chest panels 111, and abdomen panels 131 could be in fluid communication with each other and/or through main panel 150, and lower body upper leg panels 141 and lower leg panels 171 could be in communication with each other, with the upper and lower body panels not in fluid communication.

Each fluid communication zone that is to be heated and/or cooled will include internal channels, passages tubing or the like, for receiving a heat transfer medium which will be passed through the zone to provide heating or cooling. For example, the heating and cooling zones may be provided with one or more medium carrying conduits through which a heat transfer medium can flow. Alternatively, each of the heat transfer zones, may be provided with a plurality of passages forming a crisscross waffle grid pattern for the random flow of the heat transfer medium in many directions within each of the heat transfer zones as is disclosed in U.S. Pat. No. 4,149,541, issued Apr. 17, 1979 to Gammons, et al, the disclosure of which is herein incorporated by reference.

The various fluid communication zones of the heating and cooling apparati 100, 200 and 300 of the present invention include heat transfer inlets for introducing the heat transfer medium to the respective zone, and a heat transfer medium outlet through which the heat transfer medium exits the various heating and cooling zones. Generally, the heat transfer medium inlet and the heat transfer medium outlet comprise a screw fit, snap fit or other type of friction fit mechanism for engagement with tubing, piping, hosing or other type of conduit which will provide a heat transfer medium to the heat transfer zone and carry such heat transfer medium away from the heat transfer zone.

It is generally desired that at least one set of heat transfer medium inlets and the heat transfer medium outlets be positioned on one side of heating and cooling blankets 100, 200 or 300, because generally, the direction from which the fluid is provided will generally also be the direction for return. Preferably, at least one set of heat transfer medium inlets and the heat transfer medium outlets be positioned on each side of heating and cooling blankets 100, 200 or 300; because generally in the haste of positioning blankets 100, 200 or 300, care may not have been taken to determine the locations of the source of heat transfer fluid.

For example, in the embodiments as shown in FIGS. 2–5, upper body chest panels 111 and abdomen panels 131 are in fluid communication with each other with heat transfer fluid provided through tubing 211 and returning through tubing 212. The heat transfer fluid enters through tubing 211 circulates through body chest panels 111 and abdomen panels 131 and returns through tubing 212. Likewise, lower body upper leg panels 141 and lower leg panels 171 are in communication with each other. Heat transfer fluid enters through tubing 221, circulates through panels 141 and 171 and returns through tubing 222. Blankets 300 may be connected each to an external source of fluid or connectors 221 and 222 may be connected to each other with an additional set of hoses entering one blanket 300 which then connects to an external fluid source. Slightly different, non-limiting alternative positioning embodiments for tubing 211 and 212 and tubing 221 and 222 are shown in FIGS. 2–7.

It is also generally desirable that the internal fluid communication of blankets 100, 200 and 300 be suitable to allow for panels and panel extensions to be folded back on themselves without substantially impeding fluid flow. This is generally accomplished by utilizing fluid passages having suitable amount of structural integrity to resist collapse, and by using a multiplicity of passages to provide alternate fluid communication routes.

It must be understood that while one or two zones are illustrated in the heating and cooling blanket embodiment as shown in FIGS. 2–5, any desired number of zone(s) may be utilized in the practice of the present invention.

As an alternate mode of operating the heating and cooling blanket embodiment as shown in FIGS. 2–5, the outlet tubing 212 could be connected with inlet tubing 221 to convert this two zone embodiment into a single fluid communication zone embodiment.

In the practice of the present invention, the heat transfer medium utilized may be any suitable liquid, gas, gel, foam, emulsion or other flowable medium which is suitable for heat transfer. Preferably, the heat transfer medium utilized in the present invention is water. It should be understood that the heat transfer medium utilized in the present invention may include other substances, such as preservatives, bacteriacides, odorants, coloring agents, anti-corrosion agents, antioxidants, surfactants, sealants, and the like. It should be understood that the fluid communication system of the present invention may consist of a single fluid communication system having one or more various circulation loops, or the fluid communication system may consist of one or more independent systems each having one or more circulation loops. It should be understood that each of the heating/cooling zones of the heating and cooling blanket may be in fluid communication with one or more fluid circulation loops, and may share none, some or all of its fluid circulation loops with one or more of the other heating/cooling zones.

In the practice of the present invention, each of the panels and/or the optional panel extensions may be held in place by their own weight, by adhesive tape, or by the use of any suitable fastener including snaps, buttons, hooks, zippers, and hook and loop type systems a commercially available example of which includes VELCRO.

Heating and cooling apparati 100, 200 and 300 of the present invention may optionally be provided one or more access points for gaining access to a specific portion of the body of patient 10. For example, any of the panels or optional panel extensions may be provided with smaller sized openable or removable panels to allow access to patient 10 without the need to open or remove the larger panel. Each of these smaller sized panels may be secured in place by their own weight, with adhesive tape, or by any suitable fastener including snaps, buttons, hooks, zippers, and hook and loop type systems a commercially available example which includes VELCRO.

Optionally, any part of heating and cooling blanket 100, 200 or 300 may be transparent to permit visual observation of the underlying body without removal of blanket 100, 200 or 300.

The heat transfer medium of the present invention may be circulated through a closed loop heating or cooling system which is positioned adjacent to the heating and cooling apparati 100, 200 or 300 of the present invention. Methods of an apparatus for heating and cooling a circulating heat transfer medium are well known, and the present invention is not to be limited in any particular type of system. Alternatively, heat transfer medium may be provided from a larger system, such as a hospital heating or cooling water system.

It is envisioned that any suitable materials of construction may be utilized in the construction of the heating and cooling apparati 100, 200 or 300 of the present invention. In most instances, the range of operating temperatures will be those that which water is in the liquid state. It is generally preferred that the material of construction not be too resistant to bending and folding at colder temperatures. In general, the materials of construction will generally be selected from among thermoplastics, thermosets, elastomers, and rubbers.

The surface of heating and cooling blankets 100, 200 or 300 which contacts patient 10 preferably comprises an absorbent material.

It must be understood that while the heating and cooling blankets of the present invention have been illustrated only with panels for the chest, abdomen, and upper and lower legs, other panels for the head, neck, arms, hands and feet may optionally be utilized as desired or needed. Additionally, any suitable combination of panels covering any desired portion(s) of patient 10 may be utilized.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. An apparatus for providing heating and cooling to a human body having a torso having a chest area, and a back area, the apparatus comprising:
   a panel comprising left and right outer edges, and positioned there between a left portion, a middle portion, and a right portion;
   both the left portion and the right portion further comprising top and bottom portions;

the top portion and the bottom portion of the left portion are separated by a left split running from the left outer edge to a left split point on the panel which defines a portion of a left edge of the middle portion;

the top portion and the bottom portion of the right portion are separated by a right split running from the right outer edge to a right split point on the panel which defines a portion of a right edge of the middle portion;

the middle portion is suitable for contacting at least a first area of the torso, the top portion of the right portion and the top portion of the left portion can contact at least a section of second areas of the torso beyond the first area that contacts the middle portion, the bottom portion of the right portion and the bottom portion of the left portion can contact at least a section of the second areas of the torso, so a predetermined area of the torso can be exposed for medical purposes and predetermined remaining areas of torso can be covered by the apparatus; and a liquid circulation system in fluid communication with and providing liquid fluid circulation to and away from the left, middle and right portions of the panel in one circulation loop.

2. The apparatus of claim 1 wherein the body further comprises axillae with an axillary line defined as running between the axillae and wherein a section of the panel defines cradles for receiving the axillae and wherein at least a section of the panel extends above the axillary line.

3. The apparatus of claim 2 wherein the cradles have a curvilinear shape.

4. The apparatus of claim 1 wherein the body further comprises ilia with an iliac line defined as running between the ilia and wherein a section of the panel defines saddles for receiving the ilia and wherein at least a section of the panel extends below the iliac line.

5. The apparatus of claim 4 wherein the saddles have a curvilinear shape.

6. An apparatus for providing heating and cooling to a human body having a leg comprising an upper leg, a knee, and lower leg, the apparatus comprising:

a panel comprising an upper leg outer edge and a lower leg outer edge, and positioned there between a left portion, a middle portion, and a right portion;

the left portion comprises a left upper leg portion and a left lower leg portion, wherein the left upper leg portion and the left lower leg portion are separated by a first knee opening that runs from a left outer edge to a left split point on the panel which defines a portion of a left edge of the middle portion;

the right portion comprises a right upper leg portion and a right lower leg portion wherein the right upper leg portion and the right lower leg portion are separated by a second knee opening that runs from a right outer edge to a right split point on the panel which defines a portion of a right edge of the middle portion;

the middle portion is suitable for contacting a predetermined section of the leg; and a liquid circulation system in fluid communication with and providing liquid circulation to and away from the left, middle and right portions of the panel in one circulation loop.

7. The apparatus of claim 6 wherein the knee opening has a shape selected from the group consisting of circular, oval, rectangular, square, n-sided regular geometric shape, n-sided irregular geometric shape, or a combination thereof.

8. An apparatus for providing heating and cooling to a human body having a torso having a chest area, and a back area, the apparatus comprising:

a panel comprising left and right outer edges, and positioned there between a left portion, a middle portion, and a right portion;

both the left portion and the right portion further comprising parallely aligned top and bottom portions;

the top and bottom portions of the left portion are separated by a left split running from the left outer edge to a left split point on the panel which defines a portion of a left edge of the middle portion;

the top and bottom portions of the right portion are separated by a right split running from the right outer edge to a right split point on the panel which defines a portion of a right edge of the middle portion;

the middle portion is suitable for contacting at least a first area of the torso, and the top and bottom portions are suitable for contacting at least a portion of a second area of the torso beyond the first area that contacts the middle portion, so a predetermined area of the torso can be exposed for medical purposes and predetermined remaining areas of torso can be covered by the apparatus; and a liquid circulation system in fluid communication with and providing a liquid circulation to and away from the left, middle and right portions of the panel in one circulation loop.

9. The apparatus of claim 8 wherein the body further comprises axillae with an axillary line defined as running between the axillae and wherein a section of the panel defines cradles for receiving the axillae and wherein at least a section of the panel extends above the axillary line.

10. The apparatus of claim 9 wherein the cradles have a curvilinear shape.

11. The apparatus of claim 8 wherein the body further comprises ilia with an iliac line defined as running between the ilia and wherein a section of the panel defines saddles for receiving the ilia and wherein at least a section of the panel extends below the iliac line.

12. The apparatus of claim 8 wherein the saddles have a curvilinear shape.

* * * * *

UNITED STATES PATENT AND TRADEMARK OFFICE
CERTIFICATE OF CORRECTION

PATENT NO.   : 6,375,673 B1
DATED        : April 23, 2002
INVENTOR(S)  : Guy L. Clifton et al.

It is certified that error appears in the above-identified patent and that said Letters Patent is hereby corrected as shown below:

<u>Title page,</u>
Item [63], Related U.S. Application Data, change "09/065,165" to -- 09/065,156 --.

Signed and Sealed this

Seventeenth Day of September, 2002

Attest:

JAMES E. ROGAN
Attesting Officer         Director of the United States Patent and Trademark Office